United States Patent [19]

Jacob et al.

[11] Patent Number: 4,582,793
[45] Date of Patent: Apr. 15, 1986

[54] ANTI-RNA POLYMERASE I ANTIBODY TEST FOR THE DIAGNOSIS OF RHEUMATOLOGICAL DISEASES

[75] Inventors: Samson T. Jacob, Hershey; Kathleen M. Rose; Dean A. Stetler, both of Hummelstown, all of Pa.

[73] Assignee: Research Corporation, New York, N.Y.

[21] Appl. No.: 437,801

[22] Filed: Oct. 29, 1982

[51] Int. Cl.$^4$ ............... G01N 33/54; G01N 33/56; G01N 33/58
[52] U.S. Cl. ................... 435/7; 436/508; 436/509; 436/528; 436/529; 436/530; 436/531; 436/543; 436/800; 436/804; 436/808; 436/811; 436/828; 422/61
[58] Field of Search ............ 436/508, 509, 528–531, 436/543, 800, 804, 808, 811, 828; 435/7; 422/61

[56] References Cited

U.S. PATENT DOCUMENTS 4,254,097 3/1981 Rippe et al. ............ 435/7
4,340,564 7/1982 Harte et al. ............ 435/5

OTHER PUBLICATIONS

Rose et al., Proc. Natl Acad Sci. USA, 78(1981) 2833–2837.
Stetler et al., Proc. Natl Acad. Sci. USA, 78(1981) 7732–7736.
Stetler et al., Proc. Natl. Acad Sci. USA, 79(1982) 7499–7503.

Primary Examiner—Christine M. Nucker
Attorney, Agent, or Firm—Scully, Scott, Murphy & Presser

[57] ABSTRACT

A method is described for the differential diagnosis of rheumatological diseases. Sera from patients with SLE; MCTD, and RA are screened for antibodies directed against RNA polymerase II using a solid phase immunoassay. Significant levels of the antibodies were detected with sera of all SLE and MCTD patients and in 78% of the RA patients. No detectable anti-RNA polymerase I antibodies were detected in the sera of healthy individuals.

Sera from patients with SLE contained immunoglobulins directed against the S3 subunit of RNA polymerase I, as well as antibodies to the S2 or S5 subunits, RA patient's sera contained antibodies only to S3 while MCTD patients sera contained antibody to S4 in addition to antibody to the S3 and S5 subunits. The identification of specific reaction patterns of the antibodies with the individual subunits of the RNA polymerase I is indicative of a particular class of rheumatological disease.

14 Claims, No Drawings

ANTI-RNA POLYMERASE I ANTIBODY TEST FOR THE DIAGNOSIS OF RHEUMATOLOGICAL DISEASES

BACKGROUND OF THE INVENTION

This invention relates to a process and a kit including materials for diagnosing disease and particularly relates to a process for differentially diagnosing various rheumatological diseases which are characterized by the presence of autoimmune components.

Autoimmune diseases may be classified into two broad categories: systemic and organ-specific diseases. Within the systemic category, a group of disorders known as rheumatic diseases have been identified. This group includes systemic lupus erythematosus (SLE), rheumatoid arthritis (RA) and mixed connective tissue disease (MCTD). Because of the systemic nature of these diseases, patients suffering from any of the three diseases tend to present the same clinical symptoms at least during the initial stages; distinguishing among these diseases is, therefore, often quite difficult. An evaluative test which would provide for early diagnosis and discrimination of SLE, RA and MCTD would be clearly useful.

Historically, the diagnosis of SLE included, among other criteria, the identification of the lupus erythematosus (LE) cell. This cell, a polymorphonuclear leukocyte, is characterized by the presence of a large amorphous inclusion generally believed to be comprised of the nuclear contents of yet another of the patient's own white blood cells. A test based on this criterion is far from definitive in that although close to 80% of SLE patients possess the LE cell, over 70% of people who are "LE cell positive" do not have SLE.

The advent of immunofluorescent techniques allowed for the identification of a group of autoantibodies which were regularly associated with SLE. These autobodies had as their target the nuclei of the patient's own cells and became known as antinuclear antibodies (ANA). Unfortunately, even though 100% of the SLE patients displayed ANA so did 100% of R.A. and M.C.T.D. patients.

This non-specificity is not surprising when one considers the wide variety of antigenic targets which exist in the nucleus. In SLE alone, autoantibodies against such nuclear components as nucleo-protein, nuclear glycoprotein, double-stranded DNA (dsDNA), single-stranded DNA (ssDNA), double-stranded RNA (dsRNA), single-stranded RNA (ssRNA), polynucleotides, and a group of antigens known as extractable nuclear antigens (ENA) have been identified.

Although the molecular identities of some of the nuclear antigens are known (e.g. DNA:(Adams, L. E. et al. *Amer. J. of Clin. Patn.* 77(1):54–59 (1982)), RNA:(Lerner M. R. et al. *Science* Vol. 211:400–402 (1981)) and histones:(Aitkaci, A. et al *J. Imm. Meth.* 44:311–322 (1981)), the majority are defined only by their immunological or physiochemical characteristics. The identification of these antigens as proteins with specific cellular functions could lead to the elucidation of the etiologies of the autoimmune diseases as well as a method of differential diagnosis of the diseases.

Currently, a majority of the diagnostic tests for rheumatological diseases such as SLE are based upon identification of autoantibodies to DNA. For example:

U.S. Pat. No. 4,234,563 to D. R. Rippe Nov. 18, 1980 discloses a method detecting antibodies in SLE patents which are directed to DNA. The DNA is conjugated with methylated bovine serum albumn (mBSA) reacted with a serum sample, then indicated by a well-known fluorescent anti-globulin method. Further, by changing the antigen from DNA to a thymic extract, claims are drawn to detection of antibodies to extractable nuclear antigen (ENA). These ENA are not identified per se and the tests for SLE as described could not be used to detect MCTD or vise versa.

U.S. Pat. No. 3,897,212 to S. A. Leon, et al. July 29, 1975 discloses a direct radioimmunoassay for antibodies to DNA in SLE patients, by reacting a serum sample with radioactively labeled DNA and measuring the amount of radioactivity in a precipitate of the DNA and test serum.

U.S. Pat. No. 3,997,657 to B. F. Dziobkowski Dec. 14, 1976 discloses a dry slide technique for the detection of human antinuclear factor. The method involves reacting the test serum with a thymus cell extract, which had been previously affixed to a glass slide, followed by an immunofluorescent assay. No attempt was made to identify any components of the extract.

U.S. Pat. No. 4,314,987 to R. I. Morris et al. Feb. 9, 1982 discloses a method of diagnosing rheumatological diseases based upon patterns of fluorescence (i.e. homogeneous rim, speckled, nucleolar, etc.) of antinuclear antibodies, followed by testing for anti-DNA or anti-ENA antibodies. Although an ability to distinguish between SLE and MCTD is claimed, the patent essentially provides a strategy for performing and interpreting already existing tests and as such is limited in accuracy by the tests themselves. Further no data are presented to allow one skilled in the art to evaluate the efficacy of such an approach.

Contrary to teaching of U.S. Pat. No. 4,314,987 wherein nucleolar patterns of fluorescence were considered to be indefinite, the very existence of such nucleolar fluorescence (Pinnas, J L et al. *J. of Immunol.* 111(4):996–1004 (1973)) provided the impetus for the research upon which the subject invention is based.

BRIEF DESCRIPTION OF THE INVENTION

The purpose of the present invention is to provide a method for distinguishing between rheumatological diseases, such as Systemic Lupus Erythematosus (SLE) and Mixed Connective Tissue Diseases (MCTD) by analyzing a subset of autoantibodies which are routinely associated with said diseases. The autoantibodies are identified by reacting serum from a patient with SLE or MCTD with a highly purified enzyme of nucleolar origin in its native (holoenzyme) or denatured (subunit) form. The enzyme (or its subunits) serve(s) as the antigenic target for any enzyme-specific antibodies which may exist in the test sera. The antigen-antibody complex is revealed by the addition of any of a number of analytically indicatable reagents. To facilitate the addition and removal of the test reagents, the assay is performed in a solid-phase mode.

Thus, by observing the specific reaction pattern of antibodies in the test serum with various enzyme subunits a rapid, accurate differential diagnosis of SLE or MCTD may be made.

DETAILED DESCRIPTION OF THE INVENTION

To date, there has been no single reliable serological technique capable of distinguishing among different rheumatic autoimmune diseases. It is the principal object of the subject invention to provide such a methodology. It is a further object of the instant invention that it be amenable to formulation in the form of a diagnostic test kit and that the test can be prepared and performed at low cost and easily performed in a clinical laboratory.

In its preferred embodiment the invention is comprised of the following components:

A. Purified RNA polymerase I

RNA polymerases are enzymes catalyzing the transcription of DNA into RNA and would be expected to be among the many proteins in the nuclear extracts used as a source of extractable nuclear antigens (ENA). Since antinucleolar anibodies had been reported as occurring in the sera of individuals with SLE (See Pinnas J L et al supra), RNA polymerase I, a specific RNA polymerase of nucleolar origin, was selected to be the antigenic target for a subset of said antinuclear antibodies.

Anti-RNA polymerase I antibodies were detected in 100% of patients with SLE and were undetectable in 100% of normal patients. Anti-RNA polymerase antibodies were also detected in 100% of MCTD patients and in 78% of rheumatoid arthritis patients.

However, because RNA polymerase I is a complex enzyme, that is to say, the enzyme is composed of eight different polypeptides designated as: $S1(M_r=190,000)$, $S2(M_r=120,000)$, $S3(M_r=65,000)$, $S4(M_r=42,000)$, $S5(M_r=25,000)$, $S6(M_r=21,000)$, $S7(M_r=19,000)$ and $S8(M_r=18,000)$ a procedure was developed to determine which of these polypeptides contained the target antigen. Although the specificity of the anti-RNA polymerase I antibodies varied from patient to patient with respect to the individual polypeptides of the enzyme, surprisingly, distinct patterns of antibody-polypeptide interactions were observed with each type of rheumatic disease. (See Table 1).

TABLE 1

Interaction of Patients' Sera with RNA Polymerase I Polypeptides[a]

| Patient | Diagnosis | Antibodies Directed Against RNA Polymerase I Polypeptides | | | |
|---------|-----------|----|----|----|----|
|         |           | S2 | S3 | S4 | S5 |
| V.S. | RA | − | + | − | − |
| E.D. | RA | − | + | − | − |
| E.K. | RA | − | + | − | − |
| J.E. | RA | − | + | − | − |
| S.S. | RA | − | + | − | − |
| D.S. | SLE | − | + | − | + |
| V.D. | SLE | + | + | − | + |
| H.S. | SLE | + | + | − | + |
| A.S. | SLE | + | + | − | − |
| D.G. | SLE | + | + | − | − |
| S.S. | SLE | + | + | − | + |
| D.L. | SLE | + | + | − | − |
| I.S. | MCTD | − | + | + | − |
| C.C. | MCTD | − | − | + | − |
| S.B. | MCTD | − | + | + | + |
| M.B. | MCTD | − | + | + | + |

[a]The individual polypeptides of RNA polymerase I were separated by polyacrylamide gel electrophoresis under denaturing conditions and used as the antigens in a solid-phase radioimmunoassay with sera from patients determined previously to have anti-RNA polymerase I antibodies. A plus (+) and a minus (−) indicate that the antibodies directed against the particular polypeptide were and were not detected, respectively.

Specifically, sera from RA patients were found to contain antibodies directed only against the S3 polypeptide of RNA polymerase I. In contrast, SLE patients had antibodies that reacted with S2 and/or S5 in addition to S3. Neither RA or SLE patients had anti-S4 antibodies. Antibodies directed against S4 were characteristic of sera from MCTD patients which also contained anti-S3 and -S5 antibodies in some cases. These contrasting patterns of reaction with specific subunits permits the differential diagnosis of SLE and MCTD.

Although the source of the purified enzyme was from isolated nuclei of a rat tumor (Morris hepatoma 3924A) because of the phylogenetic conservation of RNA polymerases from higher eukaryotes, the rat enzyme provided a functioning target for the human antibodies.

Further, because of this said conservation, the rat enzyme should not be construed as the only source of target material. Many sources are envisioned including: human, mammals or sub-mammalian vertebrates, organs, tumors, tissue culture, or cell lines thereof or genetically engineered chimeras containing the genes for the individual RNA polymerase I subunits.

B. Analytically indicatable Reagents

Once the test serum is mixed with the target antigens the existence of a antigen-antibody reaction must be indicated. A wide variety of reagents are known for this purpose any and all of which are compatible with the subject invention. For purposes of illustration but not limitation these include: double antibody techniques involving fluoroscent-, enzyme-, ferritin-, or radioactively-labelled anti-human antibodies, $^{125}$I-/or similarly radioactively-labelled protein A from *Staphylococcus aureus*, enzyme-linked immunoassay (ELISA), or biotionized/steptavidin or avidin-linked immunoassays.

C. Buffers and Washing solutions

Since the assay involves the sequential addition of the reactants, a system of buffers to stabilize the components and remove the unreacted material is necessary. Obviously, many modifications and variations of buffering systems are possible. One such system is described in the examples which follow, however it is to be understood that the scope of the invention should not be limited to the details disclosed therein.

To summarize, the test for anti-RNA polymerase I antibodies would be performed and interpreted as follows:

(1) A patient's serum is tested against nondenatured RNA polymerase I. If the test is negative, the individual has neither SLE nor MCTD. If the test is positive, the patient may have SLE, MCTD or RA, and the second part of the test is performed.

(2) A patient's serum, determined in the first part of the test to contain anti-RNA polymerase I antibodies, is then tested for antibodies directed against each separated RNA polymerase I polypeptide. If antibodies against S4 are detected, MCTD is indicated. If antibodies against S3 and S2 and/or S5 (but not S4) are found, a diagnosis of SLE is indicated. If only anti-S3 antibodies are present, RA is indicated.

The immunoassay for antibodies directed against RNA polymerase I and its individual polypeptides, fulfills the following criteria required of a useful diagnostic procedure:

(1) The test is qualitative, i.e. positive for patients with SLE, MCTD, and RA, but negative for healthy individuals and patients with cancer. The test thus offers an advantage over tests for ANA and anti-DNA antibody since these anti-DNA antibodies can also be found in cancer patients.

(2) The test is highly specific and can distinguish between SLE, MCTD, and RA, a capability not shared by any currently available procedure.

(3) The test is quantitative and thus may be useful in monitoring the course of the disease.

(4) The test is very sensitive. Femtogram quantities of anti-RNA polymerase I antibodies can be detected. Thus, the antibodies can be found in 100% of SLE and MCTD patients.

(5) The test can be prepared and performed at low cost and, unlike the LE and ANA tests, could be easily performed in clinical laboratories that have no specialized immunology section or experience. The LE cell and ANA tests are costly and time-consuming to perform mainly because these tests require a highly-trained technician to examine several dilutions of serum from each patient under a microscope. Further, interpretation of the results is often quite subjective.

EXAMPLE I

This example illustrates a method for isolation of RNA polymerase I from one of the many cellular sources available.

Isolation of nuclei

Hepatoma-bearing rats were sacrificed 28 days after implantation of Morris hepatoma 3924A (doubling time 4.4 days). Tumors, freed of necrotic tissue, were suspended in 0.9% NaCl/0.25M sucrose. All procedures were carried out in the cold. The tumors were minced and homogenized (two strokes with a Teflon-glass homogenizer) in 12 vol. of 2.0M sucrose containing 0.25 mM spermine and 3.3 mM $MgCl_2$. The homogenate was filtered through cheesecloth and centrifuged at 40,000×g for 70 min. The pellet was resuspended (1 ml/g original tissue) in 0.34M sucrose containing 1 mM $MgCl_2$ and 0.3% (v/v) Triton X-100. The suspension was homogenized with 1–2 strokes in a Dounce homogenizer, allowed to stand for 5–10 min. at 4° C. and centrifuged at 2,000×g for 5 min. This procedure gave a high recovery of the tumor nuclei with little or no loss of enzyme activity. The Triton X-100 wash was necessary to reduce the cytoplasmic contamination and the lipid content of the tumor nuclei which interfered with subsequent extraction of the enzyme. The recovery of DNA was 1.2 mg DNA per g hepatoma.

Extraction of RNA polymerase

The purified nuclei were suspended in an alkaline buffer (1 ml/g original tissue) containing 50 mM Tris-HCl (pH 8.9), 1 mM $MgCl_2$ 0.1 mM EDTA, 2 mM dithiothreitol (DTT), 50 mM KCl, 0.5 mM phenylmethylsulfonylfluoride and 40% (v/v) glycerol. The suspension was sonicated in a Branson sonifier at full output in 15 sec. bursts monitoring for complete nuclear breakage (approx. 90 sec.). The suspension was diluted to 20% (v/v) glycerol by addition of the sonication buffer without glycerol. The extract was then precipitated with solid $(NH_4)_2SO_4$ (0.42 g/ml), allowed to stir for 45 min. and centrifuged at 80,000×g for 40 min. The precipitate was resuspended (1 ml/g) in buffer containing 50 mM Tris-HCl (pH 7.9), 25% (v/v) glycerol, 5 mM $MgCl_2$, 0.1 mM EDTA and 0.5 mM dithiothreitol (Buffer I). The suspension was dialyzed overnight against two 2-l portions of the same buffer. The suspension was then centrifuged at 80,000×g for 40 min. The viscous pellets were resuspended in Buffer I (0.6 ml/g), sonicated for 30 s and recentrifuged as above. The supernatants from both centrifugations were pooled and subjected to ion-exchange chromatography. It should be noted that this low-salt extraction procedure followed by reextraction of the chromatin, which had coprecipitated with the proteins, gave maximal yields of enzyme with minimal loss of activity.

DEAE-Sephadex Chromatography

The extracted enzyme was applied to a DEAE-Sephadex A 25 column (1.3–1.6 ml gel/g tissue) previously equilibrated in Buffer I containing 10 mM $(NH_4)_2SO_4$. After washing with 1.5 column bed volumes of Buffer I containing 10 mM $(NH_4)_2SO_4$, the enzyme was eluted with 2 column bed volumes of Buffer I containing 0.1M $(NH_4)_2SO_4$. Fractions containing enzymes were collected, pooled and dialyzed overnight against buffer containing 50 mM Tris-HCl (pH 7.9), 30% (v/v) glycerol, 0.1 mM EDTA and 0.5 mM dithiothreitol (Buffer II).

DNA-cellulose Chromatography

Pooled fractions were diluted with buffer containing 50 mM Tris-HCl (pH 7.9) and 0.5 mM DTT to reduce the glycerol to a final concentration of 15% (v/v). The diluted sample was layered onto a DNA-cellulose column, previously equilibrated in Buffer III (same as buffer I except glycerol concentration reduced to 15% (v/v)) containing 5 mM NaCl. After washing with the same buffer, enzyme was eluted with 1.5 bed volumes of Buffer III containing 0.56M NaCl. Fractions containing the enzymes were pooled.

Heparin-Sepharose Chromatography

The pooled fractions were brought to 25% (v/v) glycerol and adjusted to 0.3M salt by the addition of the appropriate amount of 3.0M $NH_4Cl$. Sample was immediately applied to heparin-Sepharose column (10.07 ml gel/g hepatoma) equilibrated in Buffer I containing 0.3M $NH_4Cl$. After washing with two bed volumes of Buffer I containing 0.3M $NH_4Cl$ the enzyme was eluted with 3 bed volumes of Buffer I containing 1M $NH_4Cl$. Fractions containing enzyme were collected and pooled.

Sucrose Density Centrifugation

The pooled fractions were dialyzed (under vacuum) overnight against Buffer I (minus EDTA) containing 0.3M KCl. Three hours prior to centrifugation, the dialysis buffer was changed to 50 mM Tris-HCl (pH 7.9), 5.0 mM $MgCl_2$, 0.3M KCl, 0.5 mM DTT, and 0.5 mM β-mercaptoethanol (Buffer IV) containing 5% (w/v) sucrose dialyzed enzyme (0.8–1.0 ml) was layered onto 10%–30% (w/v) sucrose gradient (32 ml) prepared in Buffer IV, overlayed with 1 ml Buffer IV containing 2% (w/v) sucrose and centrifuged in a DuPont TV 850 vertical rotor at 4° C. for 4 hours at 49,000 rpm. The RNA polymerase I was recovered from the gradient at 16S in a homogeneous state and was routinely used in that form.

Gel Electrophoresis (nondenaturing conditions)

To confirm its purity, the RNA polymerase I was prepared for electrophoresis by dialysis under reduced pressure against 50 mM Tris.Cl, pH 7.9; 25% glycerol 5 mM $MgCl_2$, 0.01 mM EDTA, 0.5 mM DTT, and 0.15M KCl. Electrophoresis was carried out on linear polyacrylamide (2–16%) slab gels at 70 V for 6 hours at 4° C. in 50 mM Tris 0.2M glycine, 10% glycerol, 0.1 mM DTT, 1 mM thioglycerol. The purified enzyme was then eluted from the gel.

EXAMPLE II

This example illustrates the isolation of subunits of RNA polymerase I.

RNA polymerase I obtained from sucrose density gradients centrifugation according to the procedure of Example I was denatured according to the method of Rose (*J. Biol. Chem.* 254: 10,256–261 (1979)) and placed on linear (2–10%) polyacrylamide gradient slab gels (8×7.5×0.3 cm.) at 1.5 mg of enzyme/gel. The denatured enzyme was subjected to electrophoreis under denaturing conditions as described by Laemmli (*Nature* 277:680–685 (1970)). The electrophoresis was run at 125 volts and 20 mAmp until a tracking dye reached the end of the gels. The gels were sliced into 8×0.02 cm pieces and incubated in 3 ml of 10 mM Tris-HCl (pH 7.0) buffer containing 2 mM EDTA, 50 mM NaCl, 4M Urea, 0.01M DTT for 2 hours at 25° C. The slices were rinsed in Buffer A (See Example III), homogenized, and incubated at 4° C. in 6 ml of Buffer A. After incubation the homogenized slices were pelleted at 12,000X g and the supernatant fractions containing the individual subunits were collected.

EXAMPLE III

This example illustrates one method, of the many available, for the detection of RNA polymerase I and anti-RNA polymerase I antibody complexes. RNA polymerase I, purified from isolated nuclei of a rat tumor (Morris hepatoma 3924A), according to Example I, was diluted with Buffer A consisting of 25 mM potassium phosphate (pH 7.5), 150 mM NaCl, and 0.01% (w/v) NaN$_3$ so that the final concentration of protein was 20 μg/ml. Diluted enzyme (100 μl) was placed into 400 μl capacity, flat-bottom wells (Removawell strips, Dynatech Laboratories, Inc., Alexandria, VA). After incubation at 37° C. for 3 h in a humidified chamber with gentle shaking, the solution was removed and the wells washed with Buffer A (4×100 μl). Buffer A (150 μl), containing 1% (w/v) bovine serum albumin was then placed into each well and incubated for 1 h at room temperature on a rocking platform. Following removal of the albumin-containing buffer, 100 μl of human or rabbit sera diluted 1/10 with Buffer B [50 mM Tris-HCl (pH 7.4), 150 mM NaCl, 5 mM EDTA, 0.05% (w/v) nonidet P-40, 0.1 mM phenylmethylsulfonylfluoride] were added and the wells were incubated for 1 h at room temperature and for 16 h at 4° C. The sera was removed, the wells washed with Buffer B (4×100 μl) and $^{125}$I-labelled protein A (*Staphylococcus aureus;* 30 μCi/μg) in Buffer b was added to each well (100 μl/well; 0.01 μCi/well). After incubation for 2 h at room temperature, the $^{125}$I-protein A solution was removed and the wells washed four times with 100 μl of Buffer C [50 mM Tris-HCl (pH 7.4), 1.0M NaCl, 5 mM EDTA, 0.4% (w/v) N-lauryl-sarcosine, 0.1 mM phenylmethylsulfonylfluoride]. Bound $^{125}$I-protein A was then quantitated in a gamma counter. Wells prepared in the absence of enzyme served as controls. The values obtained with individual sera in the absence of enzyme were subtracted from the values obtained in its presence (corrected cpm).

EXAMPLE IV

This example illustrates the interaction of test sera with RNA polymerase I subunits. Purified rat hepatoma RNA polymerase I. Subunits, isolated as described in Example II, were used as individual antigens in the solid-phase RIA as in Example III. Results shown in Table 2 are the mean of duplicate determinations.

TABLE 2

Interaction of Sera with RNA Polymerase I Polypeptides in the Solid-phase RIA[a]

| Subject | Diagnosis | Interaction to RNA Polymerase I Polypeptide (cpm) | | | | | |
|---|---|---|---|---|---|---|---|
| | | S1 | S2 | S3 | S4 | S5 | S6 |
| Rabbit[a] | — | 14,651 | 6,679 | 10,121 | 1,984 | 1,470 | 2,043 |
| C.K. | normal | 0 | 0 | 0 | 0 | 0 | 0 |
| S.B. | MCTD | 0 | 0 | 7,954 | 4,221 | 20,549 | 0 |
| M.B. | MCTD | 0 | 0 | 7,083 | 2,314 | 22,798 | 0 |
| E.D. | RA | 0 | 0 | 5,356 | 0 | 0 | 0 |
| E.K. | RA | 0 | 0 | 626 | 0 | 0 | 0 |
| J.E. | RA | 0 | 0 | 507 | 0 | 0 | 0 |
| D.S. | SLE | 0 | 0 | 6,704 | 0 | 12,560 | 0 |
| H.S. | SLE | 0 | 3,648 | 5,356 | 0 | 419 | 0 |
| A.S. | SLE | 0 | 2,210 | 1,644 | 0 | 0 | 0 |
| S.S. | SLE | 0 | 3,212 | 2,332 | 0 | 4,076 | 0 |

[a]Sera from a rabbit that had been immunized with RNA polymerase I was used to determine which gel slices contained polymerase polypeptides. These results were confirmed by staining a parallel gel track containing the enzyme with Coomassie blue.

We claim:

1. A method for diagnosing rheumatological disease by identifying antibodies associated with such diseases in serum from patients comprising reacting said serum with substantially purified RNA polymerase I and detecting the resultant antigen-antibody complex.

2. A method of detecting antibodies to RN polymerase I in serum comprising:
   (a) incubating a substantially purified, RNA polymerase I said polymerase being supported on a solid support, with serum containing said antibodies for a sufficient period of time thereby forming a specific antigen-antibody complex;
   (b) determining the presence of said antigen-antibody complex after removing unreacted serum therefrom, by incubating said complex with an analytically indicatable reagent for a sufficient period of time thereby forming a tertiary complex composed of antigen, antibody and analytically indicatable reagent;
   (c) determining the amount of analytically indicatable reagent in said tertiary complex, said complexed reagent being proportional to the amount of antibody in said complex.

3. A method according to claim 2, wherein said purified protein is electrophoretically pure RNA polymerase I enzyme.

4. A method according to claim 2 wherein the sources of said polymerase are cells selected from the group comprising human, mammalian, or non-mammalian vertebrate cells.

5. A method according to claim 4 wherein said cells are obtained from organs, tissue, tumors, cell lines, tissue culture or genetically engineered chimeras.

6. A method according to claim 2 wherein said analytically indicatable reagent is selected from the group consisting of fluorescein-, ferritin-, enzyme-, biotin- or radioactively-labelled anti-human antibodies, and fluorescein-, ferritin-, enzyme-, biotin- or radioactively labelled immunoglobulin binding proteins.

7. A method according to claim 6 wherein said reagent is $^{125}$I-protein A from *Staphylococcus aureus.*

8. A process for differential diagnosis of rheumatological diseases comprising reacting serum from a patient with SLE or MCTD with substantially purified subunits of RNA polymerase I, forming specific antigen-antibody complexes, identifying resultant pattern of said complexes and associating said pattern with a specific rheumatological disease.

9. A method for differential diagnosis of rheumatological diseases comprising:
   (a) incubating substantially purified subunits of RNA polymerase I enzyme, said subunits being supported on a solid support with serum from patients with systematic lupus erythrematosus or mixed connective tissue disease for a sufficient period of time thereby forming a specific antibody-antigen complex;
   (b) determining the presence of said supported complex after removing unreacted serum therefrom, by incubating said complex with an analytically indicatable reagent for a sufficient period of time thereby forming a tertiary complex compound composed of antigen, antibody and analytically indicatable reagent;
   (c) determining the amount of analytically indicatable reagent in said tertiary complex which is proportional to the amount of antibody in said complex;
   (d) identifying said subunits that have formed tertiary complexes, a specific reaction pattern being diagnostic for a particular rheumatological disease.

10. A method of claim 9 wherein said polymerase is obtained from organs, tissue, tumors, cell lines, tissue culture or genetically engineered chimeras of human, mammalian or non-mammalian vertebrate cells.

11. A method of claim 9 wherein said analytically indicatable reagent is selected from the group comprising fluorescein-, ferritin-, enzyme-, biotin-, or radioactively-labelled anti-human antibodies, and fluorescein-, ferritin-, enzyme-, biotin-, or radioactively-labelled immunoglobulin binding proteins.

12. A method of claim 11 wherein said reagent is $^{125}$I-protein A from *Staphylococcus aureus*.

13. A process according to claim 9 wherein when said reaction pattern is formed by a positive reaction of said serum with subunits S3 and S2 or S5 of RNA polymerase I such pattern is diagnostic for SLE; when a positive reaction of said test serum is formed with subunits S4 and S3 or S5 such pattern diagnostic for MCTD and when a positive reaction of said test serum is formed with subunit S3 only such pattern is diagnostic for rheumatoid arthritis.

14. A test kit for differential diagnosis of rheumatoid diseases in solid phase comprising a carrier being compartmented to receive a series of containers in close confinement which comprises a first container RNA polymerase I in native form, a second container containing RNA polymerase I in denatured form, a third container containing reaction buffers, and a fourth container containing an analytically indicatable reagent.

* * * * *